United States Patent [19]

Tzou

[11] Patent Number: 5,723,644
[45] Date of Patent: Mar. 3, 1998

[54] PHOSPHOROUS REMOVAL FROM CHLOROSILANE

[75] Inventor: Ming-Shin Tzou, Midland, Mich.

[73] Assignee: Dow Corning Corporation, Midland, Mich.

[21] Appl. No.: 846,190

[22] Filed: Apr. 28, 1997

[51] Int. Cl.$^6$ .................................................. C07F 7/08
[52] U.S. Cl. ................................. 556/466; 423/342
[58] Field of Search .................. 556/466; 423/342

[56]  References Cited

U.S. PATENT DOCUMENTS

| | | |
|---|---|---|
| 2,971,607 | 2/1961 | Caswell. |
| 3,188,168 | 6/1965 | Bradley. |
| 4,099,936 | 7/1978 | Tarancon. |
| 4,156,689 | 5/1979 | Ashby et al. ............... 556/466 |
| 4,409,195 | 10/1983 | Darnell et al.. |
| 4,481,178 | 11/1984 | Kray. |
| 5,232,602 | 8/1993 | Brink et al. ............... 210/681 |
| 5,567,836 | 10/1996 | Diaz et al. ............... 556/466 |

FOREIGN PATENT DOCUMENTS 2-153815  6/1990  Japan.

*Primary Examiner*—Paul F. Shaver
*Attorney, Agent, or Firm*—Melvin D. Fletcher

[57]  ABSTRACT

A method for the purification of chlorosilanes used for the manufacture of electronic-grade silicon and more particularly to a method for removing trace contaminants of phosphorus. The method comprises contacting a mixture comprising a chlorosilane and a phosphorus contaminant with an absorbent comprising a copper or compound of copper supported on silica.

10 Claims, No Drawings

PHOSPHOROUS REMOVAL FROM CHLOROSILANE

BACKGROUND OF INVENTION

This invention relates to purification of chlorosilanes used for the manufacture of electronic-grade silicon and more particularly to a method for removing trace contaminants of phosphorus. The method comprises contacting a mixture comprising a chlorosilane and a phosphorus contaminant with an absorbent comprising a copper or compound of copper supported on silica. The method is effective in reducing the phosphorus levels in the chlorosilane to the parts per billion range. The process can be run as a continuous or batch process.

Monocrystalline silicon wafers of extremely high purity are required for integrated circuit manufacture. The purity of the monocrystalline silicon wafers is one factor that limits the circuit density that can be formed on the silicon wafers. Therefore, as attempts are made to increase the circuit density on monocrystalline silicon wafers, there is a continuing need to reduce the impurity level in the silicon wafers.

A standard process for producing high purity monocrystalline silicon involves the chemical vapor deposition of hyper-pure chlorosilane gas, for example trichlorosilane, onto a heated silicon element. The formed silicon ingot is then float zone processed into a monocrystalline rod which can be sliced into monocrystalline silicon wafers appropriate for forming integrated circuits.

Trace contamination in the chlorosilane deposition gas is a source of contamination in monocrystalline silicon wafers. Therefore, it is desirable to reduce the trace contaminate levels in the chlorosilane deposition gas as low as possible. Many impurities such as iron, copper, and manganese, for example can be removed from the chlorosilanes by distillation. However, phosphorus content cannot be reduced to acceptable levels by simple distillation because phosphorus tends to form compounds with properties similar to those of the chlorosilane.

Previous proposed methods for the removal of phosphorus from chlorosilanes include, for example, complexing of the phosphorus compounds with selected transitional metal compounds as described in Kray, U.S. Pat. No. 4,481,178. Bradley, U.S. Pat. No. 3,188,168, describes reacting phosphorus impurities with iodine, bromine, or chlorine to form high-boiling compounds which can be separated from the chlorosilanes. Caswell, U.S. Pat. No. 2,971,607, describes the use of zeolite molecular sieves to separate the phosphorus compounds from the chlorosilanes. Darnell et al., U.S. Pat. No. 4,409,195, describe reacting chlorosilanes in the presence of oxygen at a temperature of about 60° C. to 300° C. to form Si—OH species which complex with impurities such as $PCl_3$. Brink et al., U.S. Pat. No. 5,232,602, describe a method for removing trace impurities of phosphorus by contacting liquid tetrachlorosilane with activated charcoal.

Ogi et al., JP Kokai Pat. No. Hei 2(1990)-153815, describes a method for chloropolysilane purification by contact with activated carbon. Tarancon, U.S. Pat. No. 4,099,936, describe a multi-stage process where at least one stage can comprises contacting a chlorosilane in the gas phase with activated charcoal at a temperature of minus 10° C. to 50° C. to remove impurities.

SUMMARY OF INVENTION

The present invention is a method for the purification of chlorosilanes used for the manufacture of electronic-grade silicon and, more particularly, to a method for removing trace impurities of phosphorus. The method involves contacting a mixture comprising a chlorosilane and a phosphorus contaminant with an absorbent comprising copper or a compound of copper supported on silica. The method is effective in reducing the phosphorus levels in the chlorosilane to the parts per billion range. The method can be run as a continuous or batch process.

DESCRIPTION OF INVENTION

The present invention is a method for reducing the phosphorus contamination of chlorosilanes. The method comprises contacting a mixture comprising as a major portion a chlorosilane described by formula $R_aH_bSiCl_{4-a-b}$ and as a minor portion phosphorus or a compound of phosphorus with an absorbent comprising copper or a compound of copper supported on silica. In the formula for the chlorosilane each R is independently selected and may be a substituted or unsubstituted hydrocarbon group comprising 1 to about 6 carbon atoms, a=0, 1, 2, or 3, and b=0, 1, 2, or 3.

Contacting the chlorosilane with the copper or compound of copper supported on silica can be conducted as a batch process or as a continuous process. A preferred method is a continuous process where the copper or compound of copper is supported on silica is present as a fixed-bed in an adsorption column or tower.

The chlorosilanes suitable for this method are described by formula $R_aH_bSiCl_{4-a-b}$, where each R is independently selected and may be a substituted or unsubstituted hydrocarbon group comprising 1 to about 6 carbon atoms, a=0, 1, 2, or 3 and b=0, 1, 2 or 3. More specifically, these chlorosilanes can include, for example, monochlorosilane dichlorosilane, trichlorosilane, trimethylchlorosilane, dimethylchlorosilane, methyltrichlorosilane, ethyldichlorosilane, ethyltrichlorosilane, propyltrichlorosilane, vinyltrichlorosilane, isobutyltrichlorosilane, dimethylvinylchlorosilane, methylvinyldichlorosilane, and tetrachlorosilane. Dichlorosilane and trichlorosilane are preferred chlorosilanes for the practice of this invention.

Types of silica useful in this invention include silica gels, fumed silica, amorphous silica, and precipitated silica.

The optimum particle size for the silica represents a trade-off between available surface area and the ability to create a packed column with an adequate flow rate. Generally, silicas having a particle size of about 28 to 200 mesh with a particle size distribution such that about 35 to 65% of the particles are retained on a 65 mesh screen are preferred.

The copper or compound of copper can be supported on silica using methods known in the art, such as wet impregnation. The weight of the copper or compound of copper supported on silica can be in the range of about 0.1 to 15 weight percent of the absorbent. Preferred is when the weight percent of copper or compound of copper supported on silica is in the range of about 1 to 10 weight percent of the absorbent. Most preferred is when the weight percent is in the range of about 2 to 5 weight percent of the absorbent.

Types of copper compounds useful in this invention include copper perchlorate, copper perchlorate hexahydrate, copper (I) chloride, copper (II) chloride dihydrate, and copper (II) chloride. Preferred is copper (II) chloride supported on silica.

The optimum weight of copper or compound of copper supported on silica to volume of chlorosilane contacted will depend on such factors as the amount of phosphorus in the chlorosilane, the contact temperature, chlorosilane flow-rate, the silica type and particle size, and the copper or compound of copper supported on the silica. The examples provided herein provide a general starting point from which one skilled in the art can readily determine the optimum weight of copper or compound of copper supported on silica to be employed. Preferred is when the absorbent comprising copper or a compound of copper supported on silica does not contain residual water, as this can result in chlorosilane hydrolysis. In a preferred method, the absorbent comprising copper or a compound of copper supported on silica is heated at about 300° C. to 600° C. to remove residual water prior to use. It is also believed that during heating the copper or compound of copper is reduced from the +2 oxidation state to the 0 oxidation state. The heating may be conducted in the presence of hydrogen or helium.

The temperature at which the chlorosilane is contacted with the absorbent comprising the copper or compound of copper supported on silica can be within a range of about 100° C. to 600° C. Preferred is a contact temperature within a range of about 300° C. to 500° C.

The contact time of the chlorosilane with the absorbent comprising the copper or compound of copper supported on silica will depend on the particular copper or compound of copper, silica surface area, and the chlorosilane flow-rate. Generally the contact time may be, for example, about one second to one minute.

The method of this invention is carried out by contacting the mixture comprising the chlorosilane and a phosphorous contaminant with the absorbent comprising copper or a compound of copper supported on silica and recovering the purified chlorosilane effluent. Contacting the chlorosilane with the absorbent comprising copper or a compound of copper supported on silica reduces the phosphorus and/or compound of phosphorus component contained in the chlorosilane. By "minor portion of phosphorus" it is meant those phosphorus levels typically present as contaminants in chlorosilanes used for the manufacture of electronic-grade silicon which is about 99.9 percent pure. For example, the present method is considered useful for reducing phosphorus levels initially in the chlorosilane at a parts per billion atomic (ppba). The present process is considered useful for reducing the level of phosphorus or compounds of phosphorus typically found in tetrachlorosilane and trichlorosilane for the manufacture of electronic-grade silicon. The compounds of phosphorus can be described by formula $PH_xCl_{3-x}$, where x=0, 1, 2, or 3. The process is most useful for reducing the level of $PCl_3$.

The following examples are provided to facilitate understanding of the present invention and to demonstrate the effectiveness. The examples are not intended to limit the scope of the claims provided herein.

EXAMPLE 1

Trichlorosilane spiked with $PCl_3$ to contain a level of about 143 ppba phosphorus was contacted with an absorbent comprising a compound of copper supported on silica. $CuCl_2$ was supported on Grade 12 silica (Davidson Chemical Div., W. R. Grace and Co., Baltimore, Md.) by the following method. $CuCl_2$ (4.2 gram) was dissolved in 17.2 ml of water to form a mixture. This mixture was added to 40 grams of Grade 12 silica. The absorbent comprising $CuCl_2$ supported on silica was oven dried at 100° C. for about 8 h to 10 h yielding a silica absorbent having 5 weight percent $CuCl_2$ supported on it. A 9.5 mm outside diameter quartz tube was loaded with 6 grams of the silica and heated in the presence of hydrogen gas to 600° C. for about 2 hours. The content of the quartz tube was then cooled and maintained at a temperature of about 300° C. A mixture comprising hydrogen gas and trichlorosilane was fed through the quartz tube containing the compound of copper supported on silica at a rate of 0.4 ml/s. The effluent from the quartz tube was recovered in a cold trap collection cylinder and analyzed for phosphorus using ultraviolet colorimetric analysis. No phosphorus was detected. The experimental conditions and results are recorded in Table 1.

EXAMPLE 2

The procedure of Example 1 was repeated except that the quartz tube was cooled and maintained at a temperature of about 100° C. Using ultraviolet colorimetric analysis no phosphorus was detected. The experimental conditions and results are recorded in Table 1.

EXAMPLE 3

Trichlorosilane spiked with $PCl_3$ to contain a level of about 400 ppba phosphorus was contacted with an absorbent comprising a compound of copper supported on silica. $CuCl_2$ was supported on Grade 12 silica (Davidson Chemical Div., W. R. Grace and Co., Baltimore, Md.) by the method described in Example 1. A 9.5 mm outside diameter quartz tube was loaded with 6 grams of the silica and heated in the presence of hydrogen gas to 600° C. for about 2 hours. The content of the quartz tube was then cooled and maintained at a temperature of about 400° C. A mixture comprising hydrogen gas and trichlorosilane was fed through the quartz tube containing the compound of copper supported on silica at a rate of 0.4 ml/s. The effluent from the quartz tube was recovered in a cold trap collection cylinder and analyzed for phosphorus using ultraviolet colorimetric analysis. No phosphorus was detected. The experimental conditions and results are recorded in Table 1.

EXAMPLE 4

The procedure of Example 1 was repeated except that a mixture comprising 8.5% hydrogen in helium and trichlorosilane was fed through the quartz tube containing the compound of copper supported on silica at a rate of 0.4 ml/s. Using ultraviolet colorimetric analysis no phosphorus was detected. The experimental conditions and results are recorded in Table 1.

EXAMPLE 5

Trichlorosilane spiked with $PCl_3$ to contain a level of about 400 ppba phosphorus was contacted with Grade 12 silica (Davidson Chemical Div., W. R. Grace and Co., Baltimore, Md.). A 9.5 mm outside diameter quartz tube was loaded with 6 grams of the silica and heated in the presence of helium gas to 600° C. for about 2 hours. The content of the quartz tube was then cooled and maintained at a temperature of about 550° C. A mixture comprising helium gas and trichlorosilane was fed through the quartz tube containing the silica at a rate of 0.4 ml/s. The effluent from the quartz tube was recovered in a cold trap collection cylinder and analyzed for phosphorus using ultraviolet colorimetric analysis. The phosphorus level was reduced to 1.5 ppba. The experimental conditions and results are recorded in Table 1.

EXAMPLE 6

The procedure of Example 5 was repeated and the phosphorus level was reduced to 0.7 ppba. The experimental conditions and results are recorded in Table 1.

EXAMPLE 7

The procedure of Example 6 was repeated and the phosphorus level was reduced to 1.7 ppba. The experimental conditions and results are recorded in Table 1.

TABLE 1

| Example # | Adsorbent | Temp. (°C.) | Carrier Gas | $PCl_3$ initial (ppba) | Phosphorus final (ppba) |
|---|---|---|---|---|---|
| 1 | $CuCl_2$/silica | 300 | H2 | 143 | 0 |
| 2 | $CuCl_2$/silica | 100 | H2 | 143 | 8 |
| 3 | $CuCl_2$/silica | 400 | H2 | 400 | 0 |
| 4 | $CuCl_2$/silica | 400 | 8.5% $H_2$ in He | 400 | 0 |
| 5 | silica | 550 | He | 400 | 1.5 |
| 6 | silica | 550 | He | 400 | 0.7 |
| 7 | silica | 600 | He | 400 | 1.7 |

I claim:

1. A method for reducing the phosphorus contaminant of a chlorosilane, the method comprising contacting a mixture comprising as a major portion a chlorosilane described by formula $R_aH_bSiCl_{4-a-b}$ and as a minor portion phosphorus or a compound of phosphorus with an absorbent comprising copper or a compound of copper supported on silica at a temperature in the range of about 100° to 600° C., where each R is independently selected and may be a substituted or unsubstituted hydrocarbon group comprising 1 to about 6 carbon atoms, a=0, 1, 2, or 3 and b=0, 1, 2, or 3.

2. A method according to claim 1, where the compound of phosphorus is described by the formula $PH_xCl_{3-x}$ and where x=0, 1, 2, or 3.

3. A method according to claim 1, where the compound of phosphorus is $PCl_3$.

4. A method according to claim 1, where the chlorosilane is trichlorosilane.

5. A method according to claim 1, where the chlorosilane is tetrachlorosilane.

6. A method according to claim 1, where the chlorosilane is contacted with the absorbent comprising copper or a compound of copper supported on silica at a temperature in the range of about 300° C. to 500° C.

7. A method according to claim 1, where the compound of copper is $CuCl_2$.

8. A method according to claim 1, where the weight of the copper or compound of copper supported on silica is in the range of about 0.1 to 15 weight percent of the absorbent.

9. A method according to claim 1, where the weight of the copper or compound of copper supported on silica is in the range of about 1 to 10 weight percent of the absorbent.

10. A method according to claim 1, where the weight of the copper or compound of copper supported on silica is in the range of about 2 to 5 weight percent of the absorbent.

* * * * *